United States Patent [19]

Johnson et al.

[11] Patent Number: 4,918,090

[45] Date of Patent: Apr. 17, 1990

[54] SUBSTITUTED 2-AMINBENZOTHIAZOLES AND DERIVATIVES USEFUL AS CEREBROVASCULAR AGENTS

[75] Inventors: Graham Johnson; Michael R. Pavia, both of Ann Arbor, Mich.

[73] Assignee: Warner-Lambert Company, Morris Plain, N.J.

[21] Appl. No.: 282,168

[22] Filed: Dec. 9, 1988

Related U.S. Application Data

[60] Division of Ser. No. 143,107, Jan. 25, 1988, Pat. No. 4,826,860, which is a continuation-in-part of Ser. No. 26,428, Mar. 16, 1987, abandoned.

[51] Int. Cl.$^4$ ............................................. A61K 31/425
[52] U.S. Cl. ..................................... 514/367; 514/370
[58] Field of Search ............................... 514/367, 370

*Primary Examiner*—Stanley J. Friedman
*Attorney, Agent, or Firm*—Elizabeth M. Anderson

[57] ABSTRACT

A series of substituted 2-aminobenzothiazoles and derivatives useful for treating cerebrovascular disorders are disclosed. Also disclosed is a new method for treating such disorders.

2 Claims, No Drawings

SUBSTITUTED 2-AMINBENZOTHIAZOLES AND DERIVATIVES USEFUL AS CEREBROVASCULAR AGENTS

CROSS-REFERENCE TO RELATED APPLICATION

This is a divisional of U.S. application Ser. No. 143,107 filed Jan. 25, 1988, now U.S. Pat. No. 4,826,860, which is a continuation-in-part of U.S. application Ser. No. 026,428 filed Mar. 16, 1987, now abandoned.

BACKGROUND OF THE INVENTION

The compounds of the instant invention are a series of 2-aminobenzothiazoles which are useful for treating cerebrovascular disorders.

The present invention relates to a method of using certain 2-aminobenzothiazoles and pharmaceutically acceptable salts thereof as agents in treating cerebrovascular disorders.

U.S. Pat. No. 4,370,338 covers 2-amino-6-trifluoromethoxybenzothiazole as useful as an anticonvulsant, an anxiolytic, and a hypnotic. The compound is described in Chemical Abstracts 60, 692a, 1964. Other compounds of the invention are novel.

Domino et al, in J. Pharm. Exp. Ther., 1952, 105, 486–497 and in 1953, 107, 356–367 have described the pharmacological action of substituted benzazoles as inducing paralysis.

Paris et al, in Chimie Therapeutique, 1973, 6 655–658 discloses certain 2-aminobenzothiazole derivatives as analgesics and antiinflammatories.

SUMMARY

The present invention relates to a new method for treating cerebrovascular disorders. Such disorders are described hereinbelow. The method of treatment comprises administering a therapeutically effective amount of a compound of Formula I as described hereinafter.

Stroke is one cerebrovascular disorder in particular which can be treated by the instant method. Disorders including, but not limited to, cerebral ischemia or cerebral infarction resulting from a range of conditions such as thromboembolic or hemorrhagic stroke can be treated by the instant method.

Compounds of Formula I can also be used as anesthetics especially in surgical operations where risk of cerebrovascular damage exists.

Pharmaceutical compositions are also included.

DETAILED DESCRIPTION

The instant invention concerns a new method for treating cerebrovascular disorders, such disorders are those in which excitatory amino acids, for example, glutamatic and aspartic acids, are implicated. Such disorders include cerebral ischemia or cerebral infarction resulting from a range of conditions such as thromboembolic or hemorrhagic stroke, cerebral vasospasm, hypoglycemia, cardiac arrest, status epilepticus, or cerebral trauma. Other treatments are for schizophrenia, epilepsy, neuromuscular disorders, Alzheimer's Disease, or Huntington's Disease. Still other methods of use are as analgesics and anesthetics, especially as anesthetics in surgical operations where a finite risk of cerebrovascular damage exists, for example, carotid endarterectomy.

This method of treatment comprises administering a therapeutically effective amount of a compound of Formula I or a pharmaceutically acceptable salt thereof in unit dosage form. Formula I is

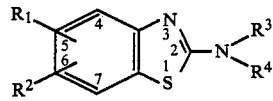

wherein
$R^1$ and $R^2$ may be the same or different and are hydrogen,
straight or branched alkyl of from one to six carbon atoms,
lower alkylaryl,
lower alkenyl,
phenyl,
$CF_3$,
hydroxy,
lower alkoxy,
lower alkylthio,
lower alkylsulphonyl,
$CF_3O$, at the six position
halogen,
nitro,
carboxy,
lower alkoxycarbonyl,
$NR^5R^6CO$,
$NR^5R^6$,
$R^5CONR^5$,
$CN$,
$NR^5R^6SO_2$,
wherein $R^5$ and $R^6$ may be the same or different and are hydrogen, lower alkyl, or aryl;
$R^1$ and $R^2$ may together form a carbocyclic or methylenedioxy ring;
$R^3$ is hydrogen;
$R^4$ is hydrogen,
lower alkyl,
lower alkyl substituted by a heterocyclic group, or substituted heterocyclic group,
methylcycloalkyl,
benzyl,
phenethyl,
phenyl,
phenyl substituted by,
halogen,
alkyl of one to six atoms,
alkoxy,
amino,
substituted amino,
carboxy,
cyano and,
nitro,
allyl
propargyl
with the proviso that $R^1$, $R^2$, and $R^3$ must be hydrogen when $R^4$ is other than hydrogen.

The term alkyl, except where otherwise stated, in alkyl per se, alkoxy, alkylaryl, alkylthio, alkylsulphonyl, alkoxycarbonyl is preferably a lower alkyl of from one to six carbon atoms and may be straight or branched.

Alkenyl means an unsaturated straight or branched chain of from one to six carbon atoms.

Aryl in alkylaryl may contain from six to ten atoms and include groups such as phenyl and naphthyl.

Alkoxy means groups such as methoxy, ethoxy, propyloxy, and the like, and alkoxycarbonyl means an ester group, for example, methyl ester, ethyl ester, benzyl ester.

The term halogen means fluorine, chlorine, bromine, and iodine.

The term carbocyclic means groups such as, for example, benzene, or cyclohexyl.

The term heterocyclic ring includes 5 and 6-membered saturated compounds such as pyrrolidine, piperidine, and heteroaromatic groups such as pyridine and thiophene.

The term substituted heterocyclic group includes substitution by lower alkyl and alkenyl such as N-methylpyrrolidine and N-allylpyrrolidine.

For $R^4$, phenyl may be substituted by halogen, alkyl of from one to six carbon atoms, alkoxy, amino, substituted amino, carboxy, cyano, and nitro.

The preferred compounds are those of Formula I wherein
$R^1$ and $R^2$ are hydrogen,
   straight or branched alkyl of from one to six carbon atoms,
   lower alkylaryl,
   alkenyl
   phenyl,
   $CF_3$,
   lower alkoxy,
   lower alkylthio,
   lower alkylsulphonyl,
   $CF_3O$ at the six position,
   halogen,
   nitro,
   $NR^5R^6$,
   $R^5CONR^5$, or
   CN;
$R^3$ is hydrogen; and
$R^4$ is hydrogen,
   alkyl,
   methylcycloalkyl, or
   benzyl,
   2-(1-methyl-2-pyrrolidinyl)ethyl,
with the proviso that $R^1$, $R^2$, and $R^3$ must be hydrogen when $R^4$ is other than hydrogen.

The more preferred compounds are:
2-aminobenzothiazole,
2-amino-6-methylbenzothiazole,
2-amino-4-methylbenzothiazole,
2-amino-6-trifluoromethylbenzothiazole,
2-amino-4-trifluoromethylbenzothiazole,
2-amino-5-trifluoromethylbenzothiazole,
2-amino-6-trifluoromethoxybenzothiazole,
2-amino-6-ethoxybenzothiazole,
2-amino-6-nitrobenzothiazole,
2-amino-4-methoxybenzothiazole,
2-amino-5-methoxybenzothiazole,
2-amino-4,6-dimethylbenzothiazole,
2-amino-6-bromobenzothiazole,
2-amino-6-chlorobenzothiazole,
2-amino-4-chlorobenzothiazole,
2-amino-6-fluoromethylbenzothiazole,
2-amino-naptho[1,2-d]thiazole,
2-ethylaminobenzothiazole,
2-[[2-(1-methyl-2-pyrrolidinyl)ethyl]amino]-benzothiazole,
2-amino-6-methylsulphonylbenzothiazole,
2-amino-4,6-difluorobenzothiazole,
2-amino-6-methylthiobenzothiazole, and
2-benzylaminobenzothiazole.

Compounds of the instant invention include solvates, hydrates, and salts of the compounds of Formula I above.

A compound of Formula I above is useful both in the free base form and in the form of acid addition salts and both forms are within the scope of the invention. The term pharmaceutically acceptable acid addition salt is intended to mean relatively nontoxic acid addition salts from either inorganic or organic acids such as, for example, hydrochloric, hydrobromic, sulfuric, phosphoric, citric, oxalic, malonic, acetic, maleic, salicyclic, ethanesulfonic, malic, gluconic, fumaric, succinic, ascorbic, methanesulfonic, benzenesulfonic, p-toluenesulfonic and the like as would occur to one skilled in the art.

Pharmaceutically acceptable inorganic and organic basic salts such as sodium, calcium, lithium, potassium, magnesium, ammonium or quaternary ammonium salts, diethylamine, and diethanolamine are also within the scope of the invention.

The acid addition salts of the basic compounds are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution. The basic addition salts are similarly prepared.

The compounds used in the invention may contain asymmetric carbon atoms. This invention includes the use of individual enantiomers or diastereomers which may be prepared or isolated by methods known in the art.

The effectiveness of the aforementioned compounds is determined by a pharmacological test procedure as described and illustrated as follows.

The procedure is entitled Combined Middle Cerebral and Ipsilateral Common Carotid Occlusion in the Rat as a Screen for Compounds Active in the Treatment of Stroke (MCAO).

Occlusion of the proximal part of the middle cerebral artery (MCA) is a common cause of stroke in man and can be accomplished surgically in experimental animals. This technique, though technically feasible in the rat is very difficult and time-consuming (Tamura, A., Graham, D. I., McCulloch, J., Teasdale, G. M., Focal Cerebral Ischemia in the Rat: 1. Description of Technique and Early Neuropathological Consequences Following Middle Cerebral Artery Occlusion. J. Cereb. Blood Flow Metab. 1:53–60, 1981). It has been reported that a distal occlusion of the MCA 5 mm from its origin at the circle of Willis does not consistently result in infarction (Coyle, P., Middle Cerebral Artery Occlusion in the Young Rat. Stroke. 13:6, 1982). We have combined distal MCA occlusion with ipsilateral common carotid ligation in an attempt to produce reproducible, focal cerebral ischemic infarcts.

Adult male Fisher (F-344) rats 250,–300 g) were anesthetized in a box containing halothane and then moved to a small animal anesthetic mask to which 1.5% halothane in room air was provided for spontaneous inspiration (Levy, D. E., Zwies, A., Duffy, T. E., A Mask for Delivery of Inhalation Gases to Small Laboratory Animals. Laboratory Animal Science, Volume 30, 5:868–870, 1980). The skin on the ventral side of the neck and the left temporal-parietal region was shaved.

An incision was made in the neck and the left common carotid artery was doubly ligated and cut between the sutures. The incision was closed with 4-0 silk. Another incision was then made behind the left eye and the skin was held back with retractors. The exposed temporalis muscle was electrocauterized (Jarit Bipolar Coagulator) and partially removed. The upper part of the lower jaw bone was also removed. Deep surgery was performed with the aid of a Zeiss OPMI 99 surgical microscope. A 1 to 2-mm diameter craniotomy was made about 1 mm anterior to where the rostral end of the zygoma fuses to the squamosal bone. To prevent the drill from going through the dura, the burr hole was not drilled completely through the skull. Bone remaining after drilling was removed with forceps. The dura was pierced and reflected with a fine probe.

At this point the rat was injected with 0.3 ml of 2% Evans blue dye in saline via the tail vein. Evans blue binds to serum albumin and will not pass the blood-brain barrier unless damage has occurred, such as damage induced by ischemia. A small hook was then positioned under the MCA and the MCA was lifted away from the cortex. A jeweler-type bipolar forceps was introduced and the MCA was electrocauterized and separated. Gelfoam was put over the craniotomy and the wound was closed with 4-0 silk. The rats were then taken off the halothane and were allowed to wake up. Total anesthesia time was typically 30 minutes. Animals undergoing this procedure (MCAO rats) awoke from anesthesia within ten minutes of breathing room air alone again and were grossly indistinguishable from unoperated rats.

On Day 2 following MCA occlusion, the rats were anesthetized with ketamine (150 mg/kg, IP) and sacrificed. Cerebral tissue fixation was initiated by perfusion of 10% neutralized, buffered formalin for five minutes. Brains were removed and stored in the fixative until analysis.

For evaluation of the extent of cerebral ischemic injury, the brains were cut coronally in three different locations. The first section was at the level where the MCA was ligated. The other two sections were 2 mm anterior and 2 mm posterior to the first. Using an aus-Jena Citoval microscope with a drawing tube and an Apple II plus computer with a Houston Instrument digitizing pad, a software routine to measure the area of the ischemic damage as indicated by the extent of Evans blue tissue extravasation was employed. The software package was purchased from R&M Biometrics (Nashville, TN) and is titled Bioquant II. From the lesion areas (mm²) obtained from the Bioquant II program, we estimated the hemispheric extent (mm³) of ischemic damage between the anterior and posterior sections by computing and adding the volume of two truncated cones.

In preliminary experiments the extent of cerebral ischemic injury was compared in MCAO and sham-operated rats. Sham-operated rats underwent an identical surgical procedure except that the bipolar electrocautery forceps were activated away from the artery but within the subarachnoid space.

The area of ischemic damage was significantly larger in the MCAO as compared to the sham-operated rats in the anterior and middle coronal sections, represented both as area of injury and area of injury as a percentage of the entire coronal section. The posterior coronal section showed a tendency toward a larger area of injury in MCAO animals relative to sham-operated controls.

Combined middle cerebral and ipsilateral common carotid artery ligation caused ischemic cerebral tissue injury which was consistently greater in extent than that injury which occurs as a result of sham operation alone. The area of injury was greatest in the anterior and middle coronal sections, which is consistent with the area of middle cerebral arterial distribution in the rat.

The Bioquant II image analysis system was used to quantitate ischemic injury as it was identified by Evans blue extravasation. The variability in extent of ischemic cerebral tissue injury in this model is small enough that it can be reasonably anticipated that successful treatment can be detected by reduction in the lesion size.

Compounds were administered in solution (the vehicle was saline, pH adjusted to be 3–5, and was without effects in the MCAO assay) by intraperitoneal injection (1.0 ml/kg body weight) 30 minutes and again 24 hours after arterial occlusions.

The duration of anesthesia is that time elapsed between administration of the test substance and the test animal regaining consciousness.

Tables I–IV below show MCAO and anesthetic activity for the disclosed compounds.

TABLE I

AMINOBENZOTHIAZOLES: [1]MCAO ACTIVITY
6-Substituted-2-Aminobenzothiazoles

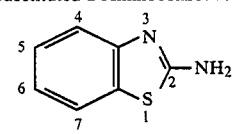

| Compound Number | R (6-position) | Dose (mg/kg) | [2]Anesthesia (Yes or No) (duration) | [3]Collateral Zone Infarct (% of Control) | [4]Hemispheric Infarct (% of Control) |
|---|---|---|---|---|---|
| 1 | —H | 10 | No | 36 | 61 |
|   |    | 30 | Yes (2 hr) | 11 | 47 |
| 2 | —SMe | 10 | — | 72 | 88 |
|   |    | 30 | — | 100 | 106 |
| 3 | —Me | 10 | Yes (2–3 hr) | 54 | 77 |
|   |    | 30 | Yes (4–6 hr) | 14 | 51 |
| 4 | —SO₂Me | 10 | No | 77 | 83 |
|   |    | 30 | No | 58 | 86 |
| 5 | —Cl | 3 | No | 77 | 83 |
|   |    | 10 | No | 58 | 86 |
|   | —Cl | 10 | No | 23 | 63 |

TABLE I-continued

AMINOBENZOTHIAZOLES: [1]MCAO ACTIVITY
6-Substituted-2-Aminobenzothiazoles

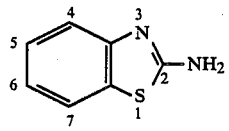

| Compound Number | R (6-position) | Dose (mg/kg) | [2]Anesthesia (Yes or No) (duration) | [3]Collateral Zone Infarct (% of Control) | [4]Hemispheric Infarct (% of Control) |
|---|---|---|---|---|---|
|  |  | 30 | Yes (>3 hr) | 31 | 66 |
| 6 | —OEt | 10 | No | 94 | 115 |
|  |  | 30 | No | 16 | 59 |
| 7 | —Br | 10 | No | 69 | 88 |
|  |  | 30 | Yes (>5 hr) | 59 | 68 |
| 8 | —NO$_2$ (Example 3) | 10 | No | 92 | 93 |
|  |  | 30 | Yes (4 hr) | 24 | 62 |
| 9 | —OCF$_3$ | 3 | No | 117 | 99 |
|  |  | 10 | No | 43 | 66 |
|  |  | 15 | No | 42 | 82 |
|  |  | 30 (N = 2) | Yes (1–2 hr) | 0 | 44 |
| 10 | —CF$_3$ | 3 | No | 156 | 131 |
|  |  | 10 | No | 51 | 53 |
| 11 | —F | 10 | No | 42 | 76 |
|  |  | 30 | Yes (<4 hr) | 96 | 96 |

TABLE II

AMINOBENZOTHIAZOLES: [1]MCAO ACTIVITY
4-Substituted-2-Aminobenzothiazoles

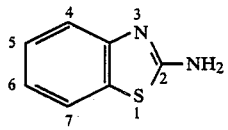

| Compound Number | R (4-position) | Dose (mg/kg) | [2]Anesthesia (Yes or No) (duration) | [3]Collateral Zone Infarct (% of Control) | [4]Hemispheric Infarct (% of Control) |
|---|---|---|---|---|---|
| 12 | 4,6-dimethyl | 10 | No | 91 | 79 |
|  |  | 30 | No | 68 | 76 |
| 13 | —OMe | 3 | No | 85 | 90 |
|  |  | 10 | Yes (>5 hr) | 115 | 121 |
| 14 | —Me | 10 | No | 69 | 72 |
|  |  | 30 | No | 40 | 54 |
| 15 | —Cl | 10 | Yes (2 hr) | 63 | 75 |
|  |  | 30 | Yes (>5 hr) | 15 | 51 |
| 16 | —CF$_3$ | 10 | No | 63 | 99 |
|  |  | 30 | Yes | 15 | 61 |
| 17 | 4,6-difluoro | 10 | No | 137 | 139 |
|  |  | 30 | Yes | 105 | 115 |

TABLE III

AMINOBENZOTHIAZOLES: [1]MCAO ACTIVITY
5-Substituted-2-Aminobenzothiazoles

| Compound Number | R (5-position) | Dose (mg/kg) | Anesthesia (Yes or No) (duration) | Infarct (% of Control) | [4]Hemispheric Infarct (% of Control) |
|---|---|---|---|---|---|
| 18 | —OMe | 10 | No | 124 | 117 |
|  |  | 30 | No | 54 | 82 |
| 19 | —CF$_3$ | 10 | No | 48 | 63 |
|  | (Example 7) | 30 | No | 53 | 79 |
| 20 | —4,5-(C$_4$H$_4$) | 30 | Yes | 81 | 92 |

TABLE IV

AMINOBENZOTHIAZOLES: [1]MCAO ACTIVITY
2-Substituted-benzothiazoles

| Compound Number | R | Dose (mg/kg) | [2]Anesthesia (Yes or No) (duration) | [3]Collateral Zone Infarct (% of Control) | [4]Hemispheric Infarct (% of Control) |
|---|---|---|---|---|---|
| 21 | —NHEt (Example 5) | 10 | No | 62 | 71 |

TABLE IV-continued

AMINOBENZOTHIAZOLES: [1]MCAO ACTIVITY
2-Substituted-benzothiazoles

| Compound Number | R | Dose (mg/kg) | [2]Anesthesia (Yes or No) (duration) | [3]Collateral Zone Infarct (% of Control) | [4]Hemispheric Infarct (% of Control) |
|---|---|---|---|---|---|
|  |  | 30 | No | 116 | 89 |
| 22 | —NHCH₂Ph(Example 6) | 10 | No | 56 | 76 |
|  |  | 30 | No | 98 | 89 |
| 23 | 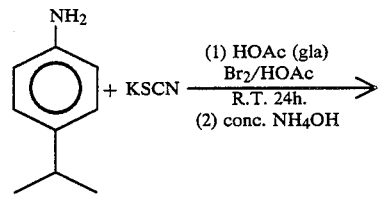 | 10 | No | 66 | 84 |
|  |  | 30 | No | 18 | 72 |

[1]MCAO Activity: Compounds were given IP in solution 30 minutes after stroke onset and again 24 hours later.
[2]Anesthesia:
Yes - Rats showed impaired consciousness and lack of righting reflex after dosing.
No - Rats may have been ataxic but could right themselves and responded to noxious stimuli after dosing.
[3]Collateral Zone Infarct: Posterior section of ipsilateral cerebral hemisphere - infarct is measured in $mm^2$ and presented as a percentage of respective historical control sections.
[4]Hemispheric Infarct: Estimated total hemispheric volume measured in $mm^3$ and presented as a percentage of historical controls.

Collateral Zone (C) and Hemispheric (H) Infarct Volumes are expressed as Percent of Historical Control Rats (N=30) and were measured quantitatively after combined middle cerebral and ipsilateral carotid artery occlusion (MCAO) according to the protocol described above. The collateral zone (posterior cerebral tissue section) was assessed as a specific indicator of injury to an area of the brain away from the arterial occlusion site. The hemispheric volume was an assessment computed from multiple cerebral tissue sections to provide an overall impression of infarct size.

For the therapeutic uses described above, the usual mammalian dosage range for a 70 kg human subject is from 1 to 2100 mg per day or 0.01 mg to 30 mg per kg of weight per day; optionally in divided portions. Determination of the proper dosage for a particular situation is within the skill of the art.

Pharmaceutical compositions of the compound of the present invention or its salts are produced by formulating the active compound in dosage unit form with a pharmaceutical carrier. Some examples of dosage unit forms are tablets, capsules, pills, powders, aqueous and nonaqueous oral solutions, and suspensions and parenteral solutions packaged in containers containing either one or some larger number of dosage units and capable of being subdivided into individual doses. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerine; sorbitol; polyethylene glycol; water; agar; alginic acid; isotonic saline, and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits, but for practical purposes it is preferably present in a concentration of at least 10% in a solid composition and at least 2% in a primarily liquid composition. The most satisfactory compositions are those in which a much higher proportion of the active ingredient is present.

Routes of administration of the subject compound or its salts are oral, parenteral, transdermal, or intranasal. For example, a useful intravenous dose is between 0.01 and 10.0 mg/kg. A preferred intravenous dose is 0.1 to 5.0 mg/kg. A still further preferred dose is 0.1 to 1.0 mg/kg. A useful oral dose is 0.01 to 30 mg/kg. A preferred oral dose is 0.1 to 10 mg/kg. A further preferred dose is 1.0 to 5.0 mg/kg. All of the above are as would occur to a person skilled in the art.

The following examples are provided to enable one skilled in the art to practice the invention. These examples are not intended to limit the scope of the invention in any way but rather to be illustrative thereof. Many of the compounds of the invention are known and in some cases commercially available.

EXAMPLE 1

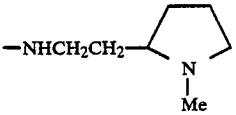

To a stirred mixture of 4-isopropylaniline (10.0 g, 0.074 mol) and potassium thiocyanate (14.38 g, 0.148 mol) in 100 mL of glacial acetic acid was added dropwise, bromine (11.83 g, 0.074 mol) in 25 mL glacial acetic acid, over 0.5 hours. The reaction mixture was stirred vigorously for 24 hours at room temperature. The reaction mixture was poured over ice, and the solution made basic to pH 10 with concentrated ammonium hydroxide to produce a yellow precipitate. The 2-amino-6-isopropylbenzothiazole was collected by filtration and recrystallized from toluene (50% yield, m.p. 123°–124° C.).

| calc. | C | 64.46 | H | 6.29 | N | 14.57 | S | 16.68 |
| found | C | 62.44 | H | 6.32 | N | 14.60 | S | 16.65 |

EXAMPLE 2

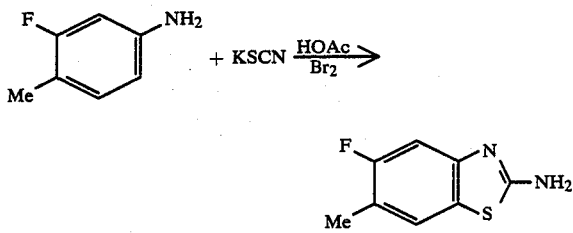

To a Stirred mixture of 9.3 g (0.074 mol) of 3-fluoro-4-methylaniline and 14.4 g (0.148 mol) potassium thiocyanate in 50 mL glacial acetic acid was added dropwise 11.8 g (0.074 mol) of bromine. The solution was stirred at room temperature for 18 hours. The reaction solution was poured over ice and basified to pH 10 with concentrated ammonium hydroxide to yield a precipitate. The solid, 2-amino-5-fluoro-6-methylbenzothiazole was collected by filtration and recrystallized from ethanol or toluene.

EXAMPLE 3

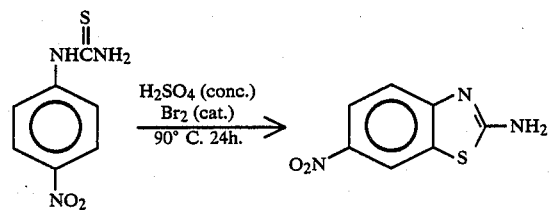

To a stirred mixture of 1-(4-nitrophenyl)-2-thiourea (15.0 g, 0.076 mol) in 20 mL of concentrated sulfuric acid was added dropwise, bromine (0.61 g, 0.004 mol) in 10 mL concentrated sulfuric acid over 0.5 hours. The reaction mixture was heated to 90° C., and stirred vigorously for 24 hours. The reaction was cooled slowly to room temperature and quenched by pouring over ice. The solution was made basic to pH 10 with concentrated ammonium hydroxide, producing a yellow solid. The 2-amino-6-nitro-benzothiazole was filtered and recrystallized from ethanol (85% yield, m.p. 246°–247° C.).

| calc. | C | 43.07 | H | 2.58 | N | 21.53 | S | 16.43 |
| found | C | 42.71 | H | 2.46 | N | 21.58 | S | 16.79 |

EXAMPLE 4

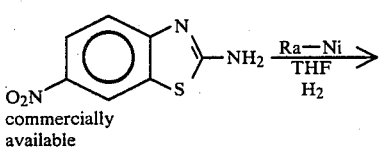
commercially available

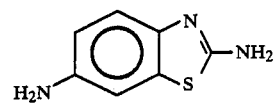

To a solution of 2-amino-6-nitrobenzothiazole (10 g, 0.051 mol) in 100 mL of tetrahydrofuran was added 3.0 g Raney-nickel active catalyst. The reaction mixture was hydrogenated until hydrogen consumption ceased. The reaction mixture was filtered through a Celite pad and the solution was concentrated under reduced pressure to produce a brown solid. The solid was recrystallized from toluene, yielding 2,6-diaminobenzothiazole (50% yield, m.p. 202°–203° C.).

| calc. | C | 50.88 | H | 4.27 | N | 25.43 | S | 19.41 |
| found | C | 50.71 | H | 4.42 | N | 25.43 | S | 19.80 |

EXAMPLE 5

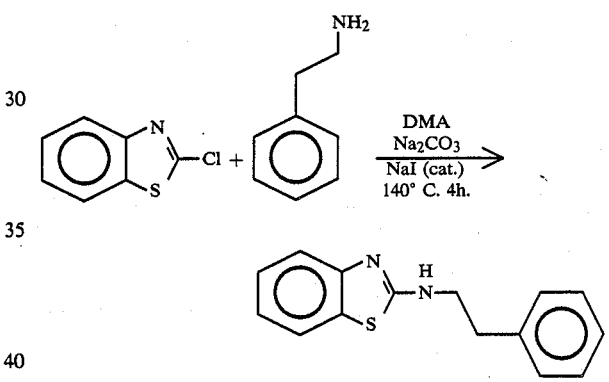

To a stirred mixture of 2-chlorobenzothiazole (13.3 g, 0.077 mol), sodium carbonate (9.77 g, 0.092 mol) and sodium iodide (0.22 g, 0.0015 mol) in 15 mL N,N-dimethylacetamide, was added phenethylamine (10.24 g, 0.084 mol) in one portion. The reaction mixture was heated to 140° C., stirred vigorously for four hours and allowed to cool slowly to room temperature. At this time the reaction was quenched with water producing a brown solid. The N-(2-phenethyl)-2-benzothiazolamine was collected by filtration and recrystallized from di-isopropyl ether (8% yield, m.p. 143° C.).

| calc. | C | 70.80 | H | 5.55 | N | 11.02 | S | 12.61 |
| found | C | 70.80 | H | 5.76 | N | 11.05 | S | 12.82 |

EXAMPLE 6

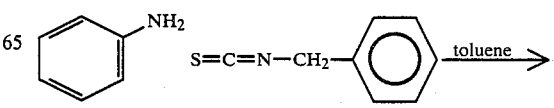

-continued

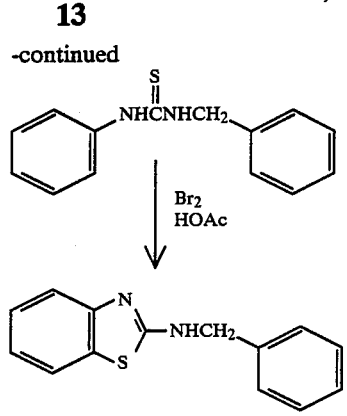

(As illustrative of literature procedures, a further general method for the preparation of the disclosed compounds given here)

To a stirred solution of 74.6 g (0.5 mol) of benzylisothiocyanate in 500 mL toluene was added dropwise 46.6 g (0.5 mol) of aniline. The solution was refluxed 18 hours. After cooling, the reaction mixture was concentrated under reduced pressure. The residue was recrystallized from an appropriate solvent to yield N-phenyl-N'-benzylthiourea. Isothiocyanates which are not commercially available may be prepared from aliphatic or aryl primary amines by the following methods: Kurita and Iwakura, Org. Synth. 59, 195; Jochims, Chem. Ber. 101, 1746 (1968); or Castro, Pena, Santos, and Vega, J. Org. Chem. 49, 863 (1984).

To a stirred solution of 12.1 g (0.05 mol) of N-phenyl-N'-benzylhiourea in 150 ml of glacial acetic acid was added dropwise 8.0 g (0.05 mol) of bromine in 60 mL of glacial acetic acid. The reaction was poured into 10 volumes of water and made basic with concentrated ammonium hydroxide. A solid precipitated from the aqueous solution and was filtered. The solid could be recrystallized from an appropriate solvent to yield N-benzyl-2-benzothiazolamine.

EXAMPLE 7

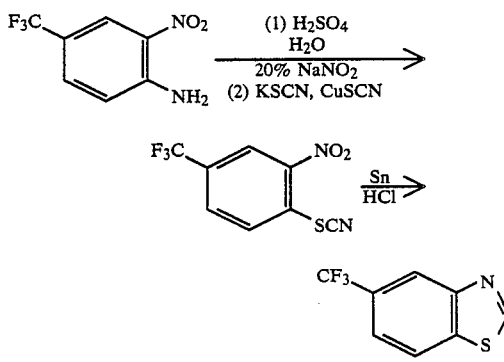

3-Nitro-4-thiocyanatebenzotrifluoride

To a stirred solution of 20.6 g (0.10 mol) 4-amino-3-nitrobenzotrifluoride in 30 mL conc. H₂SO₄ and 30 mL H₂O at 0° C. was added dropwise 37.5 mL 20% sodium nitrite. The mixture was stirred for 90 minutes at 0°–5° C. Potassium thiocyanate (10 g in 20 mL H₂O) was added dropwise and stirred 15 minutes. The reaction was poured into a vigorously stirred slurry of 18 g (0.148 mol) copperthiocyanate in 60 mL H₂O. Gas evolution began and the mixture foamed. The reaction was stirred two hours at 3° C. and then heated to 70° C. for 20 minutes. The reaction was cooled to 25° C. and stirred an additional 18 hours. The solution was filtered and the water was extracted with toluene (3×100 mL). The toluene layer was dried (Na₂SO₄), filtered, and concentrated under reduced pressure to yield a purple oil. The product was purified by silica gel chromatography. The column was eluted initially with hexane followed by hexane/CH₂Cl₂ (7:3) to yield an oil which was crystallized from heptane to yield a yellow solid, m.p. 72°–73° C.

| | | | | | | |
|---|---|---|---|---|---|---|
| calc. | C | 38.71 | H | 1.22 | N | 11.29 |
| found | C | 38.62 | H | 1.17 | N | 11.10. |

2-amino-5-trifluoromethylbenzothiazole hydrochloride

To a vigorously stirred solution of 4.0 g (0.16 mol) 3-nitro-4-thiocyanatebenzotrifluoride in 50 mL conc. HCl was added 16.0 g (0.135 mol) granulated tin over one hour. The reaction changed from an orange to very pale yellow to white. The reaction was stirred at 25° C. for 20 h. The reaction solution was diluted with H₂O (250 mL) and conc. NH₄OH was added dropwise. The product precipitated along with the tin salts. The solid was filtered and boiled in CHCl₃ (3×200 mL). The aqueous layer was extracted with CHCl₃. All the CHCl₃ washings were combined, dried (MgSO₄), filtered, and concentrated under reduced pressure to yield a dark brown solid. The crude benzothiazole was dissolved in hot Et₂O and filtered. To the filtrate was added a solution of freshly prepared Et₂O/HCl. The product precipitate was filtered and washed with Et₂O to yield a white solid m.p. 255°–257° C.

| | | | | | | |
|---|---|---|---|---|---|---|
| calc. | C | 37.73 | H | 1.98 | N | 11.00 |
| found | C | 37.50 | H | 2.33 | N | 10.76 |

We claim:

1. A method for treating cerebrovascular disorders which comprises administering to a patient in need thereof a therapeutically effective amount of a compound of the formula

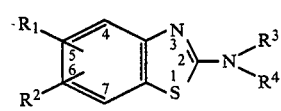

or a pharmaceutically acceptable salt thereof in unit dosage form wherein

R¹ and R² are hydrogen

R₃ is hydrogen;

R₄ is lower alkyl substituted by a substituted or unsubstituted pyrrolidine, piperidine, pyridine or thiophene wherein the substituents are a straight or branched alkyl or alkenyl of from one to six carbon atoms.

2. A method for treating cerebrovascular disorders which comprises administering to a patient in need thereof a therapeutically effective amount of 2-[[2-(1-methyl-2-pyrrolidinyl)ethyl]amino]-benzothiazole.

* * * * *